(12) United States Patent
Lass

(10) Patent No.: US 9,758,388 B2
(45) Date of Patent: Sep. 12, 2017

(54) DEVICE AND METHOD FOR WATER FILTRATION USING RECYCLED MEDICAL FILTERS

(75) Inventor: Yoram Lass, Tel-Aviv (IL)

(73) Assignee: Nufiltration Ltd., Caesarea (IL)

( * ) Notice: Subject to any disclaimer, the term of this patent is extended or adjusted under 35 U.S.C. 154(b) by 403 days.

(21) Appl. No.: 13/376,614

(22) PCT Filed: Jun. 7, 2010

(86) PCT No.: PCT/IL2010/000448
§ 371 (c)(1),
(2), (4) Date: Dec. 7, 2011

(87) PCT Pub. No.: WO2010/143184
PCT Pub. Date: Dec. 16, 2010

(65) Prior Publication Data
US 2012/0074060 A1 Mar. 29, 2012

Related U.S. Application Data

(60) Provisional application No. 61/184,809, filed on Jun. 7, 2009, provisional application No. 61/312,255, filed on Mar. 10, 2010.

(51) Int. Cl.
*C02F 1/44* (2006.01)
*B01D 65/02* (2006.01)
*A61M 1/16* (2006.01)

(52) U.S. Cl.
CPC ............ *C02F 1/444* (2013.01); *A61M 1/168* (2013.01); *B01D 65/02* (2013.01); *B01D 65/022* (2013.01); *C02F 1/44* (2013.01); *Y02W 10/37* (2015.05)

(58) Field of Classification Search
CPC ..... A61M 1/168; B01D 65/022; B01D 65/02; B01D 63/043; B01D 63/046; C02F 1/1444; C02F 1/44; Y02W 10/37
USPC ............ 210/645, 646, 650, 651, 232, 321.6, 210/321.72, 323.2, 340
See application file for complete search history.

(56) References Cited

U.S. PATENT DOCUMENTS

| | | | |
|---|---|---|---|
| 4,707,268 A * | 11/1987 | Shah et al. ................ | 210/650 |
| 4,707,335 A | 11/1987 | Fentress et al. | |
| 5,238,563 A * | 8/1993 | Smith et al. ............ | 210/321.74 |
| 5,897,832 A | 4/1999 | Porter | |
| 6,214,231 B1 | 4/2001 | Cote et al. | |

(Continued)

FOREIGN PATENT DOCUMENTS

| | | |
|---|---|---|
| CN | 1202116 | 12/1998 |
| CN | 1259975 | 6/2006 |
| CN | 101208119 | 6/2008 |

(Continued)

OTHER PUBLICATIONS

Translation of Notification of Office Action Dated Sep. 9, 2013 From the State Intellectual Property Office of the People's Republic of China Re. Application No. 201080035084.2.

(Continued)

*Primary Examiner* — John Kim

(57) ABSTRACT

A water filtration system uses previously used medical filters, such as dialysis filters, for water purification. After medical use the filters are cleaned and sterilized and mounted singly or in groups so as to receive input water under pressure. The system produces sterile filtered water.

15 Claims, 15 Drawing Sheets

(56) References Cited

U.S. PATENT DOCUMENTS

| | | | |
|---|---|---|---|
| 6,655,394 | B1 | 12/2003 | Tanaka et al. |
| 2007/0007193 | A1* | 1/2007 | Uchi et al. ............... 210/321.79 |

FOREIGN PATENT DOCUMENTS

| | | |
|---|---|---|
| DE | 19538818 | 4/1997 |
| DE | 10111104 | 10/2002 |
| EP | 0864334 | 9/1998 |
| EP | 2008704 | 12/2008 |
| FR | 1245751 | 11/1960 |
| WO | WO 97/40860 | 11/1997 |
| WO | WO 2010/143184 | 12/2010 |

OTHER PUBLICATIONS

Translation of Search Report Dated Sep. 9, 2013 From the State Intellectual Property Office of the People's Republic of China Re. Application No. 201080035084.2.
International Preliminary Report on Patentability Dated Dec. 22, 2011 From the International Bureau of WIPO Re. Application No. PCT/IL2010/000448.
Communication Pursuant to the Results of the Partial International Search Dated Aug. 26, 2010 From the International Searching Authority Re. Application No. PCT/IL2010/000448.
International Search Report and the Written Opinion Dated Nov. 4, 2010 From the International Searching Authority Re. Application No. PCT/IL2010/000448.
Translation of Notification of Office Action Dated Jan. 31, 2013 From the State Intellectual Property Office of the People's Republic of China Re. Application No. 201080035084.2.
Translation of Search Report Dated Jan. 31, 2013 From the State Intellectual Property Office of the People's Republic of China Re. Application No. 201080035084.2.
Communication Pursuant to Article 94(3) EPC Dated Nov. 9, 2012 From the European Patent Office Re. Application No. 10731813.1.
Communication Pursuant to Article 94(3) EPC Dated Sep. 2, 2013 From the European Patent Office Re. Application No. 10731813.1.
Decision of Rejection Dated Apr. 24, 2014 From the State Intellectual Property Office of the People's Republic of China Re. Application No. 201080035084.2 and Its Translation Into English.
Communication Pursuant to Article 94(3) EPC Dated Jun. 3, 2014 From the European Patent Office Re. Application No. 10731813.1.
Notification of Office Action Dated Sep. 9, 2014 From the State Intellectual Property Office of the People's Republic of China Re. Application No. 201080035084.2 and Its Summary in English.
Communication Pursuant to Article 94(3) EPC Dated Jan. 16, 2015 From the European Patent Office Re. Application No. 10731813.1.
Notification of Office Action Dated Feb. 12, 2015 From the State Intellectual Property Office of the People's Republic of China Re. Application No. 201080035084.2.
Patent Examination Report Dated Nov. 13, 2015 From the Australian Government, IP Australia Re. Application No. 2010258227.
Patent Examination Report Dated May 30, 2016 From the Australian Government, IP Australia Re. Application No. 2010258227.
Requisition by the Examiner Dated Jul. 19, 2016 From the Canadian Intellectual Property Office Re. Application No. 2,764,361.
Office Action Dated Sep. 4, 2016 From the Israel Patent Office Re. Application No. 216822 and Its Translation Into English.

* cited by examiner

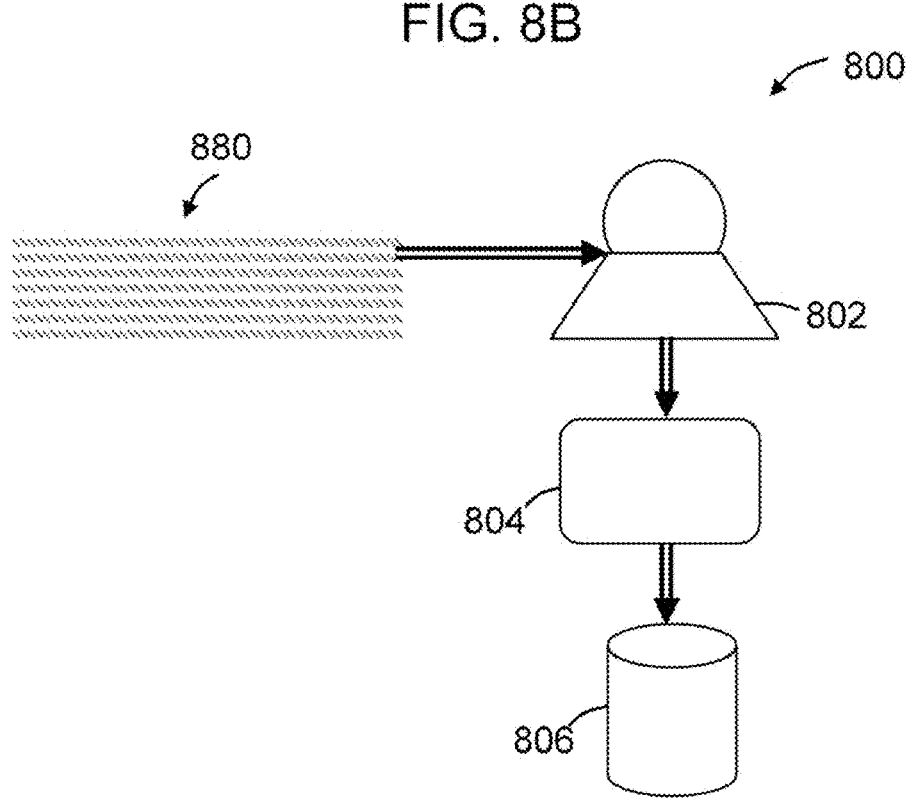
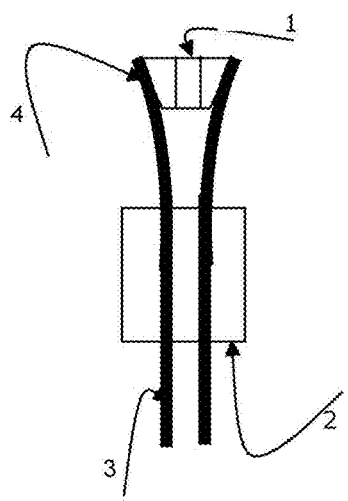

DEVICE AND METHOD FOR WATER FILTRATION USING RECYCLED MEDICAL FILTERS

RELATED APPLICATIONS

This application is a National Phase of PCT Patent Application No. PCT/IL2010/000448 having International filing date of Jun. 7, 2010, which claims the benefit of priority off U.S. Provisional Patent Application Nos. 61/184, 809 filed on Jun. 7, 2009, and 61/312,255 filed on Mar. 10, 2010. The contents of the above applications are all incorporated herein by reference.

FIELD OF THE INVENTION

The present invention, in some embodiments thereof, relates to water filtration and to reuse, in water filtration systems, of medical filters previously used during medical treatments and a connection thereof to water filtration systems.

BACKGROUND OF THE INVENTION

Waste water, surface water, storm water, ground water and sea water are frequently contaminated with the fecal material of man or other animals. *Cryptosporidium oocysts* (protozoan infections), *E. coli* and *Vibrio cholerae* (bacterial infections), and Hepatitis A (viral infections) are but a few examples. Water filtration and water purification are required in many situations. In addition, these waters may include colloidal materials, which can destroy expensive Reversed Osmosis ("RO") membranes used in water purification and particularly in desalinization. The fouling of these expensive membranes must be prevented by pretreatment of water scheduled to undergo reversed osmosis treatment.

Ultrafiltration ("UF") can be used, for example, for production of tertiary effluent from secondary effluent in municipal waste water treatment plant, such as for "polishing" sand filter tertiary effluent and, for example, for water pretreatment in reversed osmosis applications such as the desalination of sea water and brackish water. Ultrafiltration is a separation process using filter membranes having pore sizes in the range of 0.1 micron (100 nanometer) to 0.001 micron (1 nanometer). UF membranes are used to treat surface water, storm water, ground water, seawater and waste water as either primary treatment or as pretreatment in reversed osmosis desalination plants, or other types of desalinization plants. In these and other applications, UF filters are used in water filtration to remove high molecular-weight substances, colloidal materials, organic and inorganic polymeric molecules, and pathogens.

However, UF water filters are expensive.

Large water treatment plants typically use 500-1000 UF filters at a cost of many millions of dollars (including support systems). One such filter typically costs more than a thousand dollars. For example, at retail prices current at the time of filing of this application, Applied Membrane Model M-UB8040PES 8"×40" UF PES Membrane 10,000 MWCO (Molecular Weight Cut Off) costs is $1544 (without the pressure tank). Hydronautics' Hydrocap UF filter sells for $2550.

Apart from the UF membranes per se, water filtration apparatus typically requires various tubes and couplings (e.g. quick release) as used in the industry or described in publications such as DE 8612396, JP 2007195851, U.S. Pat. No. 4,923,226, US 2009/227954, DE 29803673, or WO 2007/049053.

SUMMARY OF THE INVENTION

The present invention, in some embodiments thereof, relates to use of recycled medical filters, such as filter units designed for dialysis treatment, for water filtration. Potentially, such use can reduce cost of water filtration and purification while optionally or alternatively gaining benefit from expensive medical grade equipment which would otherwise be discarded, causing great waste and/or disposal problems and creating an environmental burden.

In some embodiments according to the invention a water filtration system comprises a medical filter such as a dialysis filter which, after having been used for medical treatment of a patient, possibly multiple times, is optionally cleaned, optionally sterilized, and connected to a water flow system so as to produce filtered and substantially clean water free of extraneous materials including pathogens. In some embodiments a plurality of filters, which may be medical filters such as dialysis filters, cleaned and sterilized, are connected in parallel to a water flow system so as to provide high throughput, thereby constituting a filter group suitable for commercial and industrial applications. In some embodiments filters of the group are connected through cut-off valves enabling to conveniently remove individual filters for cleaning or replacement during ongoing water filtration by the filter group as a whole. In some embodiments a water filtration system comprises a plurality of such groups of filters, which may be connected through cut-off valves enabling to isolate a selected filter group from the water filtration system, e.g. for cleaning or repair or replacement, during ongoing water filtration by the system.

According to an aspect of some embodiments of the present invention there is provided a water filtration system comprising at least one filtration unit which is a sterilized medical filters previously used for medical treatment.

According to some embodiments of the invention the system comprises a plurality of filtration units connected in parallel.

According to some embodiments of the invention the filtration unit is an ultrafiltration filter previously used for dialysis.

According to some embodiments of the invention the previously used medical filter is sterilized according to at least the US ANSI/AAMI/RD47:2008 standard prior to being used for water filtration.

According to some embodiments of the invention the system comprises at least 20 filtration units connected in parallel.

According to some embodiments of the invention at least some of the filtration units are organized in filter groups connected in parallel, each of the groups comprising a plurality of filtration units connected in parallel to a common input connection and a common output connection operable to connect the unit to the system and to disconnect it therefrom.

According to some embodiments of the invention at least some of the groups are connectable in parallel to an input connector and an output connector, thereby forming a supra-group, which supra-group is connectable to the system.

According to some embodiments of the invention the system comprises valves operable to isolate at least some of the filter groups, enabling to disconnect the isolated group from the system while other connected groups of the system are actively filtering water.

According to some embodiments of the invention the filter comprises a membrane having pores sized between 0.1 micron and 0.001 micron in diameter.

According to an aspect of some embodiments of the present invention there is provided a method for providing a plurality of water connections for a plurality of dialyzers, comprising:
  (a) providing a pipe and a plurality of dialyzers;
  (b) forming a plurality of holes on an edge of the pipe;
  (c) inserting end portions of the dialyzer in the pipe; and
  (d) administering self-leveling adhesive into the pipe.

In some embodiments, the adhesive is administered such that the adhesive spreads around the end portions of the dialyzers inside the pipe.

According to an aspect of some embodiments of the present invention there is provided method for connecting a dialyzer to a water treatment apparatus, comprising:
  (a) providing a dialyzer;
  (b) fitting a tube to the dialyzer inlet and/or outlet; and
  (c) connecting the tube to water.

In some embodiments, the dialyzer is a discarded hemodialyzer.

In some embodiments, the tube is a flexible tube.

In some embodiments, fitting comprises with matching.

In some embodiments, the method further comprises inserting a conical hollow member at one end of the flexible tube thereby dilating the tube about the end thereof.

In some embodiments, the method further comprises inserting the flexible tube into a flexible hollow member.

In some embodiments, the method further comprises inserting the flexible tube, with the conical member and the flexible member into the inlet and/or outlet of the dialyzer, dilated end of the flexible tube facing the dialyzer.

In some embodiments, the method further comprises pulling the flexible tube outwardly of the inlet and/or outlet through the hollow of the flexible member while maintaining the position of the flexible member and pushing the dilated end of the flexible tube in the hollow of the flexible member, thereby dilating the hollow of the flexible member and forming a sealing contact with the inlet and/or outlet of the dialyzer.

In some embodiments, at least or any of the tube or adapters are of low cost and/or commodity items and/or made of commodity items.

According to an aspect of some embodiments of the present invention there is provided an apparatus for water treatment, comprising a dialyzer fitted with a low cost tube of a different diameter at an inlet and/or outlet thereof, providing a connection for connecting the dialyzer to water.

In some embodiments, the dialyzer is a discarded hemodialyzer.

In some embodiments, the low cost tube is fitted in the inlet and/or outlet of the dialyzer by one or more low cost adapters.

In some embodiments, the low cost tube and/or adapters are commodity items and/or made of commodity items.

In some embodiments, the low cost adapters are less expensive than a connector of hemo-dialyzer.

According to an aspect of some embodiments of the present invention there is provided a method for connecting first tube to a wider second tube, comprising:
  (a) providing a first tube having a dilation at one end thereof;
  (b) providing a second tube wider than the first tube having an opening;
  (c) inserting the first tube with the dilated end into the second tube; and
  (d) pulling out the first tube, thereby pressing the dilated end at the wall of the second tube.

In some embodiments, the first tube is dilated by inserting a member wider than the first tube at the end thereof.

In some embodiments, the diameter of the second tube narrows towards the opening thereof.

In some embodiments, the first tube is pressed on the wall of the second tube via a flexible member surrounding the first tube about the end thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, sensors such as pressure sensors, chlorine sensors, turbidity sensors and the like, and a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse or a voice-control module are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 8B schematically illustrate a setup for water filtration system which does not require electric power for operation, according to an embodiment of the present invention;

FIG. 9 schematically shows a connection assembly of a flexible small diameter tube, equipped with a connection device and inserted into a hollow member, according to an embodiment of the present invention;

DESCRIPTION OF SPECIFIC EMBODIMENTS OF THE INVENTION

Figure 1:
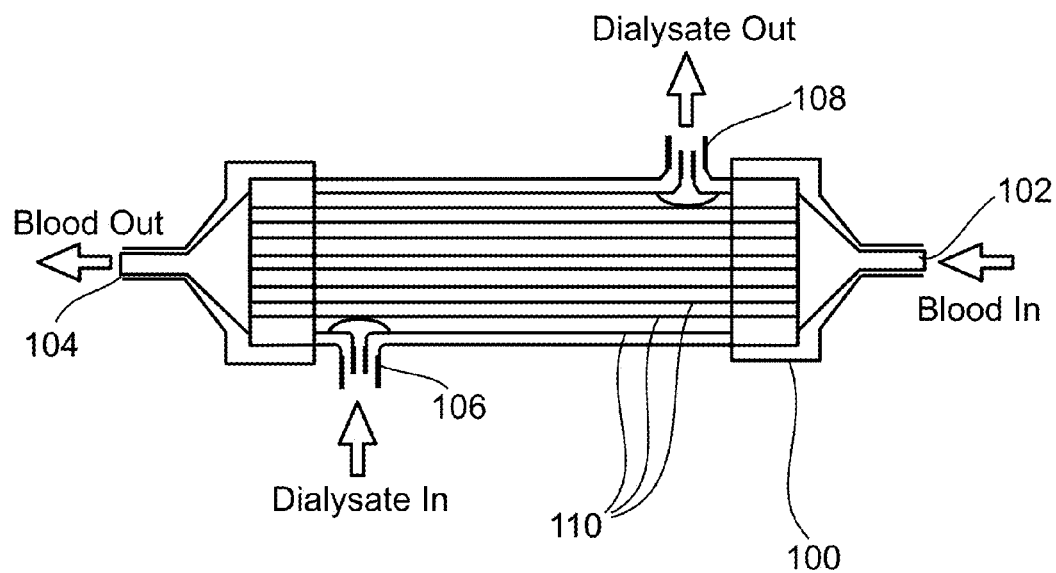
FIG. 1 is a simplified schematic of a dialysis filter showing its traditional use according to prior art.

The present invention, in some embodiments thereof, relates to a water filtration system, and more particularly, but not exclusively, to a water filtration system comprising a medical filter previously used in a medical procedure, or rejected from such use during manufacture for such use and a connection thereof to water filtration systems. In some embodiments, filter units designed for dialysis treatment, after being cleaned and sterilized, are used singly or in groups to filter water for drinking, for conditioning prior to reversed osmosis desalinization and/or for other agricultural or industrial uses or water or other fluid treatments. In this manner, expensive medical equipment which would otherwise be discarded, causing great waste and creating an environmental burden, is used instead to provide high-quality water filtration at a cost possibly lower than that of the water filtration methods known to prior art.

Every year, many millions of expensive ultrafiltration membranes (sometimes referred to herein as "UF" membranes) are discarded after a single use in dialysis units around the world. A smaller but significant number are discarded after multiple medical uses. Many are high grade, high flux polysulfone UF membranes. (such as Fresenius FX-80 membrane). As an example which provides some indication of the quantities involved, it is estimated that about 2000 filters and several kilometers of tubing are discarded every day in Israel, with a population of around 7 million. One might extrapolate to an estimate of a quantity of about 100,000 such filters thrown away every day, around the world. They are expensive pieces of fine, medical grade equipment, but once they have been used they are treated as garbage, medical waste, an expense to their users and an environmental burden to society.

The MWCO (Molecular Weight Cut Off) of the artificial kidney dialyzer such as Fresenius FX80 is about 20,000. All or almost all known pathogens are filtered out by this dialyzer. Consequently use of such filters to filter water for drinking or other industrial or agricultural purposes is an option, once they have been cleaned of materials left behind after their initial medical use. Converting a waste material into beneficial use is exceptional as customarily used dialyzers are disposed of as potentially hazardous material.

In some dialysis units (mainly in the USA), dialyzers are reused over and over again, under the US ANSI/AAMI/RD47:2008 standard. (See details of the American National Standard: ANSI/AAMI RD47:2008 "Reprocessing of Hemodialyzers" at www.marketplace.aami.org/eseries/scriptcontent/docs/Preview%20Files%5CRD470806_preview.pdf This accepted standard was developed for economic reasons, to permit reuse of this expensive and valuable equipment. According to the standard reuse procedure, after cleaning the dialyzer with water and bleach, dialyzers are re-sterilized by filling the filter with a germicide solution, usually 4% formaldehyde solution, for 24 hours. For details relating to this process and/or to the above mentioned standard the reader is referred to AAMI, the Association for the Advancement of Medical Instrumentation at www.aami.org, ANSI, the American National Standards Institute at www.ansi.org, a Federal Register article §405.2150 "Condition: Reuse of hemodialyzers and other dialysis supplies", accessible at www.edocketaccess.gpo.gov/cfr_2002/octqtr/pdf/42cfr405.2160.pdf. Example of a dialyzer reprocessing system is the RENATRON® 11 100 Series, an FDA-approved hemodializer reprocessing system, to be seen at www.minntech.com/renal/products/renatron/index.html.

Since cleaning and sterilization according to the above-mentioned standard is considered sufficient to prepare a used dialysis filter for re-use in direct contact with the bloodstream of a human patient, it may be appreciated that it may be considered at least sufficient for general water treatment applications. Indeed, a considerably less stringent standard may be considered appropriate for cleaning the used dialyzers—for example—using regular drinking water rather than sterile water during the cleaning of the used dialyzer for the purpose of the present invention.

In some embodiments a water filtration system comprises a medical filter such as a blood filter, for example a dialysis filter, which, after having been used for medical treatment of a patient, is optionally cleaned, optionally sterilized, and connected to a water flow system so as to produce filtered and substantially clean water free of pathogens and other extraneous materials. Optionally, the water filtration system also comprises tubing used in the original medical usage, and prepared for re-use together with the filter to which it was connected.

In some embodiments a plurality of filters, which may be medical filters such as dialysis filters, cleaned and sterilized, are connected in parallel to a water flow system so as to provide high throughput, thereby constituting a filter group suitable for commercial and industrial applications. Such a filter group may comprise all re-used filters, or a combination of re-used filters and other filters.

In a prototype model, 40 cylindrical dialysis filters, each approximately 5 cm in diameter and less than 30 cm long, are connected together in parallel and packed in an enclosure whose dimensions are approximately 60 cm×40 cm×33 cm. The used dialysis filters, after cleaning and sterilization according to the standard mentioned above, were connected in parallel using inexpensive parts (including, for example, manifolds designed for use in agricultural irrigation systems) and also using cleaned and sterilized tubing and connectors which were part of the original dialysis equipment and were discarded along with the dialysis filters. This prototype model, with a few addition inexpensive parts, produces more than 75 cubic meters per day of clean purified water. The cost of commercial water filter systems with similar capacity is substantially greater than that of the prototype.

Exemplary embodiments of the present invention can play a significant role in the worldwide fight against water bound diseases, water pollution and water shortage. Among a variety of possible applications, some embodiments are suited for use in underdeveloped countries: an embodiment described below can use a single reconditioned dialysis filter to provide filtered sterile water to an entire village, and the system can run without electricity. Other embodiments are suited to municipal and industrial waste water treatment plants of large size and modern design. Some embodiments are suited to the pretreatment of water being prepared for further treatment by reversed osmosis, for example in desalination plants for treating salt water and brackish water.

Some embodiments are suitable for treating river water and rainwater or storm water runoff, others for sewage, and indeed embodiments of the invention can be used to treat water from almost any kind of water source. The potential benefits for providing clean water for human needs are many and varied.

At the same time, use of some embodiments of the invention provides another type of human service: dialysis filters and other medical filters, contaminated by human blood and other substances, are discarded every day in enormous quantities. These objects constitute a biohazard. Processes for disposing of them appropriately are relatively costly, and doing so in a manner which is environmentally sound is not trivial. However, when reconditioned and used in embodiments such as those described herein, the filters and tubing which are normally considered and handled as troublesome garbage under methods of prior art become a valuable but inexpensive commodity with potential for bringing great benefit to the environment and to human health.

In some embodiments filters of the group are connected through cut-off valves enabling to conveniently remove individual filters for cleaning or replacement during ongoing water filtration by the filter group as a whole. In some embodiments a water filtration system comprises a plurality of such groups of filters, which may be connected through cut-off valves enabling to isolate a selected filter group from the water filtration system, e.g. for cleaning or repair or replacement, during ongoing water filtration by the system. In some embodiments a flow rate meter or pressure sensor or particle counter or particle detector or particle trap may be used to determine if a filter or group of filters is failing or clogging.

It is noted that although exemplary embodiments of the invention refer to the use of a dialysis filter, these embodiments are exemplary only, and the invention is not limited to this specific type of filter. Indeed, any medical filter having a molecular cut off weight sufficiently low to filter all or most known pathogens may be used in place of the dialysis filter presented in the exemplary embodiments described herein.

In some embodiments, hemo-dialyzers are connected to water (e.g. water source or drain) and/or to parts of a water treatment apparatus by extension tubes. In some embodiments, such as for convenience, the extension tube is flexible and narrower then the inlets or outlets of the hemo-dialyzer and the connection of an extension tube comprises width or diameter adaptation or conversion (fitting, matching).

In some embodiments, low cost components and/or tubes are used for connection hemo-dialyzers in a water treatment apparatus rather than more expensive devices such as quick release devices of a hemo-dialysis machine. Thus, in some embodiments, discarded hemo-dialyzers connected with low cost components provides water treatment much less expensive than comparable off-the-shelf or other commercial systems or component, and in some cases provide water treatment to regions and/or population that cannot afford commercial systems. Additionally, in some embodiments, water treatment with discarded hemo-dialyzers connected with low cost components can be used without electricity, where pressure is provided such as by gravity or manual pump.

An aspect of some embodiments of the invention relates to a method of attaching two tubes of different sizes, for example for low pressure systems. In an exemplary embodiment of the invention, the tubes are connected using an intermediate fitting which is expanded so that it seals against the inner surface of the larger diameter tube, while carrying the smaller diameter tube in a lumen within it. Optionally, the expansion is by providing a widening section on the smaller diameter tube and retracting said smaller diameter tube into said intermediate fitting, so that the widening section widens the intermediate fitting.

Using the method described above allows connecting and/or fitting tubes of different diameters or widths or of various diameter ratios, optionally of imprecise and/or inconsistent and/or varying diameters. In some embodiments of the invention, the method allows dispensing of complex tube connectors, and connecting dialyzers to water treatment system with low cost components potentially suitable for water treatment for impoverished environment and/or population.

As used herein, the term 'low cost' implies generally available (e.g. as a commodity) items or products or products made by simple process or of generally available material, optionally as surplus of other products (e.g. of plumbing).

As also used herein, the term 'impure' water denotes water to be treated and the term 'water source' denotes a supply or vessel of impure water and the term drain' or 'drainage' denotes collection or collecting vessel of treated water.

For simplicity of clarity, without limiting the term 'dialyzer' is used herein to denote a hemo-dialyzer, or another membrane filtration device having similar or comparable properties operational and mechanical properties.

Before explaining at least one embodiment of the invention in detail, it is to be understood that the invention is not necessarily limited in its application to the details of construction and/or the arrangement of the components and/or methods set forth in the following description and/or illustrated in the drawings and/or the Examples. The invention is capable of other embodiments or of being practiced or carried out in various ways.

It is expected that during the life of a patent maturing from this application many relevant ultrafiltration filters and other dialysis modules will be developed and the scope of the terms "filter" and "dialysis filter" are intended to include all such new technologies a priori.

The terms "comprises", "comprising", "includes", "including", "having" and their conjugates mean "including but not limited to".

The term "consisting of means "including and limited to".

As used herein, the singular form "a", "an" and "the" include plural references unless the context clearly dictates otherwise.

In discussion of the various Figures described herein below, like numbers refer to like parts.

The drawings are generally not to scale.

For clarity, non-essential elements were omitted from some of the drawings.

Referring now to the drawings, FIG. 1 is a simplified schematic of a dialysis filter 100, showing its traditional use according to prior art. Blood is caused to circulate between entrance 102 and exit 104, while a dialysate is caused to circulate between entrance 106 and exit 108. Capillaries 110 extend between blood entrance 102 and blood exit 104. Urea molecules and other small molecules pass through the capillary walls, which prevent passage of large molecules, thus cleansing the blood of urea while preserving large-molecule blood contents intact.

Figure 2:
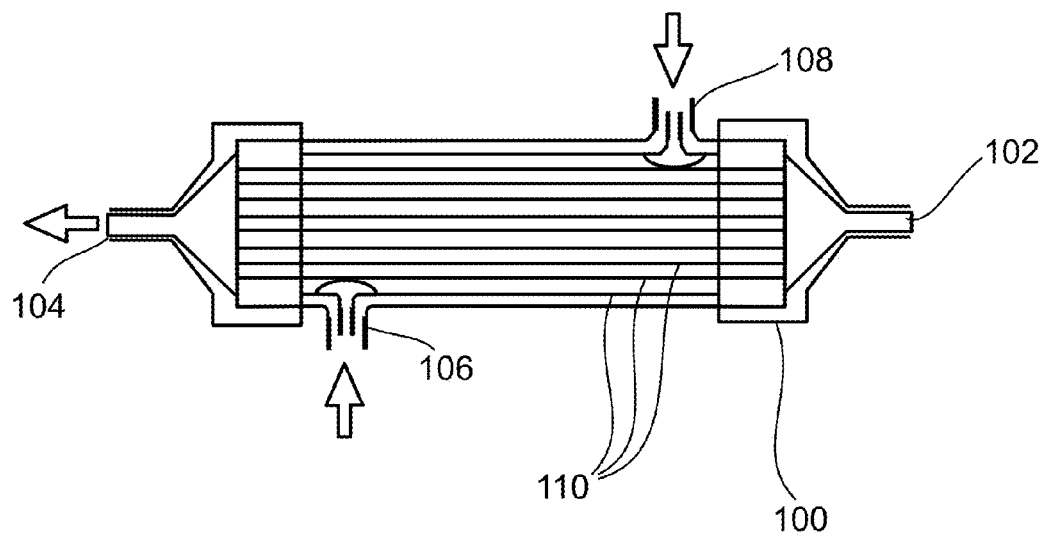
FIG. 2 is a simplified schematic of a dialysis filter showing its use according to an embodiment of the present invention.

FIG. 2 is a simplified schematic of dialysis filter 100, used according to an embodiment of the present invention. In an exemplary embodiment, unfiltered water is provided under pressure at 106 and 108, and water which has passed through the filtering capillary walls of capillaries 110 is withdrawn at 104. It is to be understood however that this specific configuration is exemplary only, and that other connections using the filtering capacity of filter 100 are possible, so long as unfiltered water is applied under pressure at one side of a filtering membrane and filtered water is drawn off from the other side of that membrane. In practice it has been found convenient and effective to supply water under pressure at 106 and 108, and to withdraw filtered water at 102 or 104. A relative pressure of 0.5 BAR has been found sufficient to produce effective flow, though other pressures may be convenient depending on specific details of the implementation. In some embodiments, an 'outside-in' filtering as described above is employed, where, in some embodiments, 'inside out' filtering may be employed.

It is noted that as the filter is used, large molecules will accumulate in the pressure tank surrounding the capillary system and will eventually reduce water flow through the filter. Accordingly it has been found useful to occasionally reverse the flow of water, supplying water (preferably filtered water, to preserve the cleanliness of the system) under pressure at e.g. 102, so as to reverse the flow within the capillaries. This has the effect of freeing accumulated material, which is then flushed from the filter. In a prototype version it has been found that a reverse flow of two minutes every two hours is sufficient to free the filter of accumulated material and preserve good flow-through. Chlorine or similar materials may be added to the back wash fluid to facilitate cleaning and prevent fouling of membranes. Air scouring (air bubbles) may also be introduced to aid this process.

Figure 3:
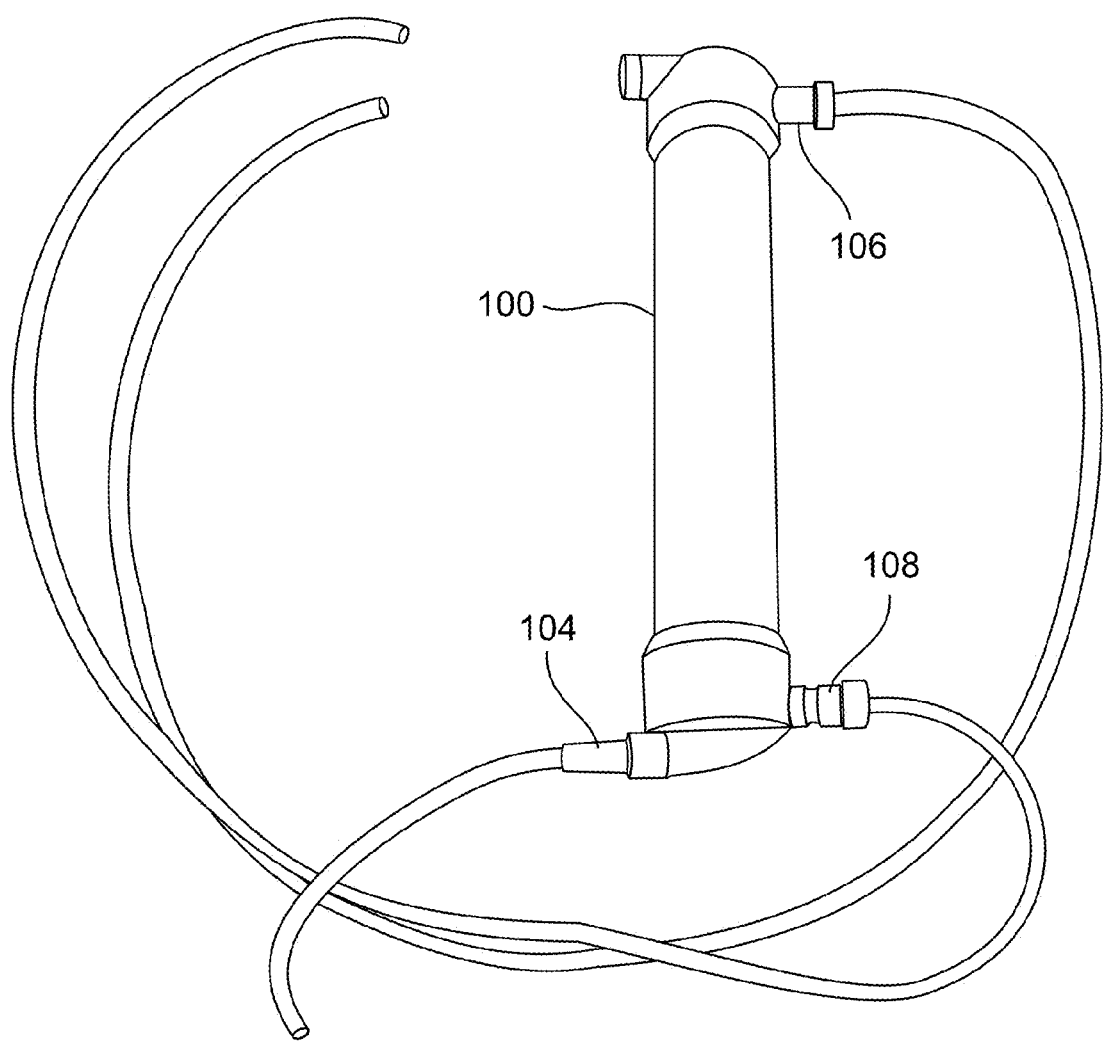
FIG. 3 is an external view of a dialysis filter with connections as required according to an embodiment of the present invention.

FIG. 3 is an external view of filter 100, showing the connections presented schematically in FIG. 2.

Figure 4:
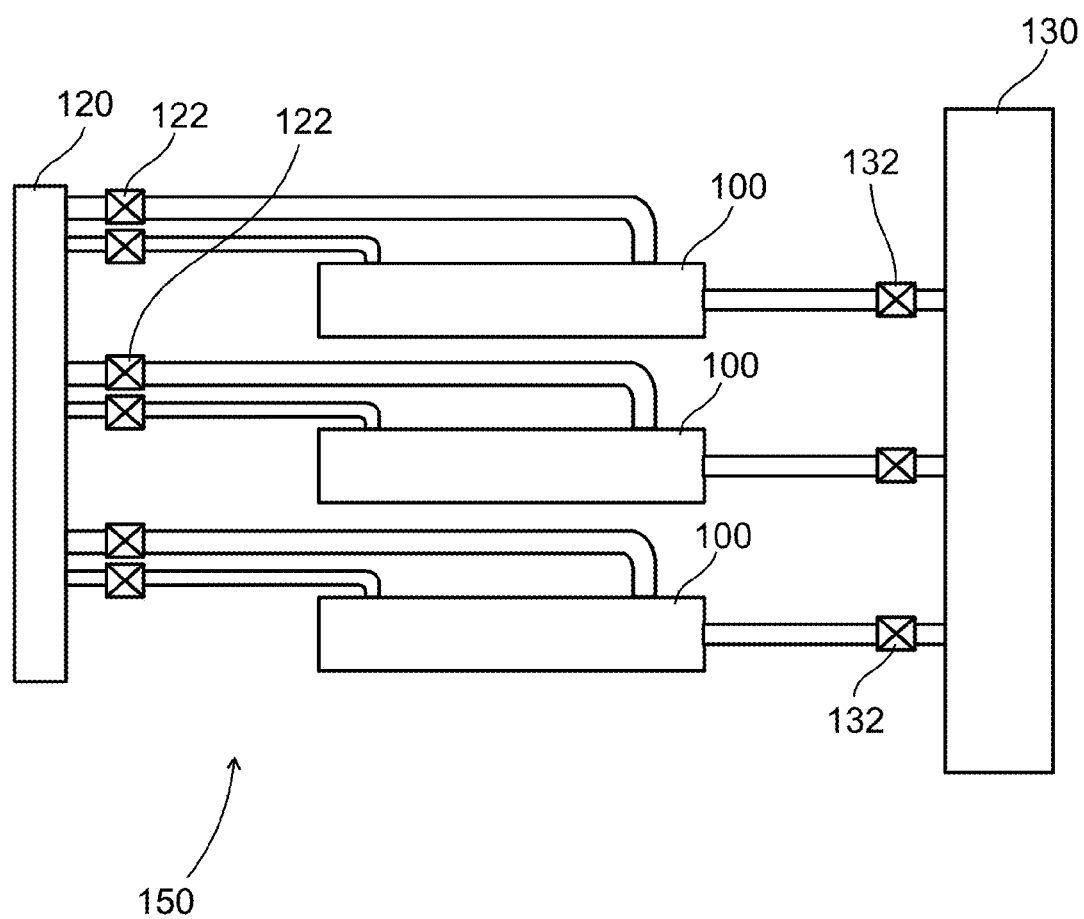
FIG. 4 is a simplified schematic of a group of filters, according to an embodiment of the present invention.

FIG. 4 is a simplified schematic of a group of filters, according to an embodiment of the present invention. In an exemplary embodiment, filter group 150 comprises an input manifold 120 which supplies unfiltered pressurized water to a plurality of filters 100, and an output manifold 130 which collects filtered water therefrom. Optionally, input valves 122 and output valves 132 may be provided to enable easy and rapid isolation of an individual filter 100 for repair, cleaning, or replacement. If valves 122 and 132 are present, then individual filters 100 can be removed or replaced while group 150 is proceeding to filter water.

Figure 5:
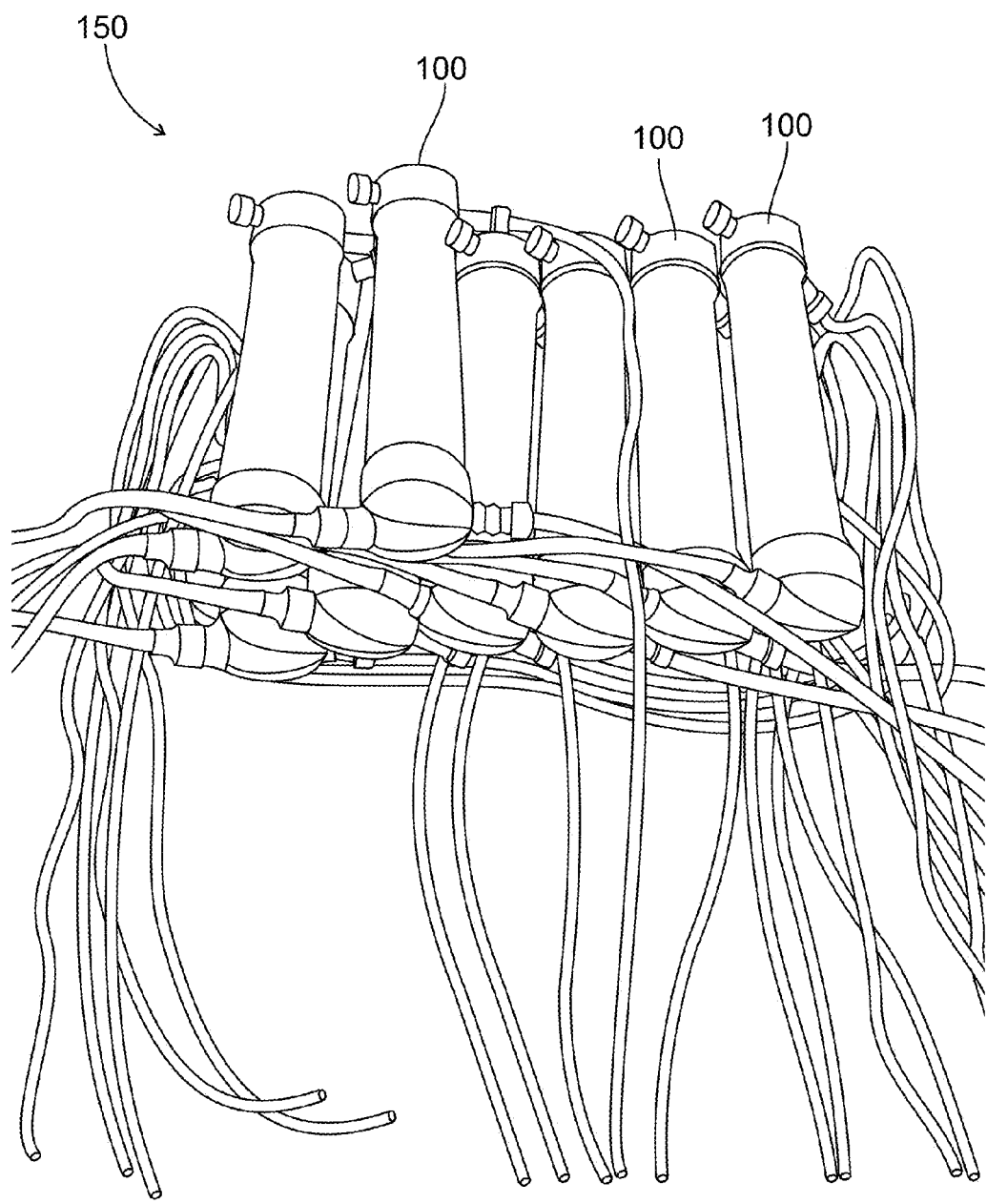
FIG. 5 is an external view of a group of filters, as described schematically in FIG. 4, according to an embodiment of the present invention.

FIG. 5 is an external view of a group of filters 100, as described schematically in FIG. 4, according to an embodiment of the present invention.

Figure 6A:
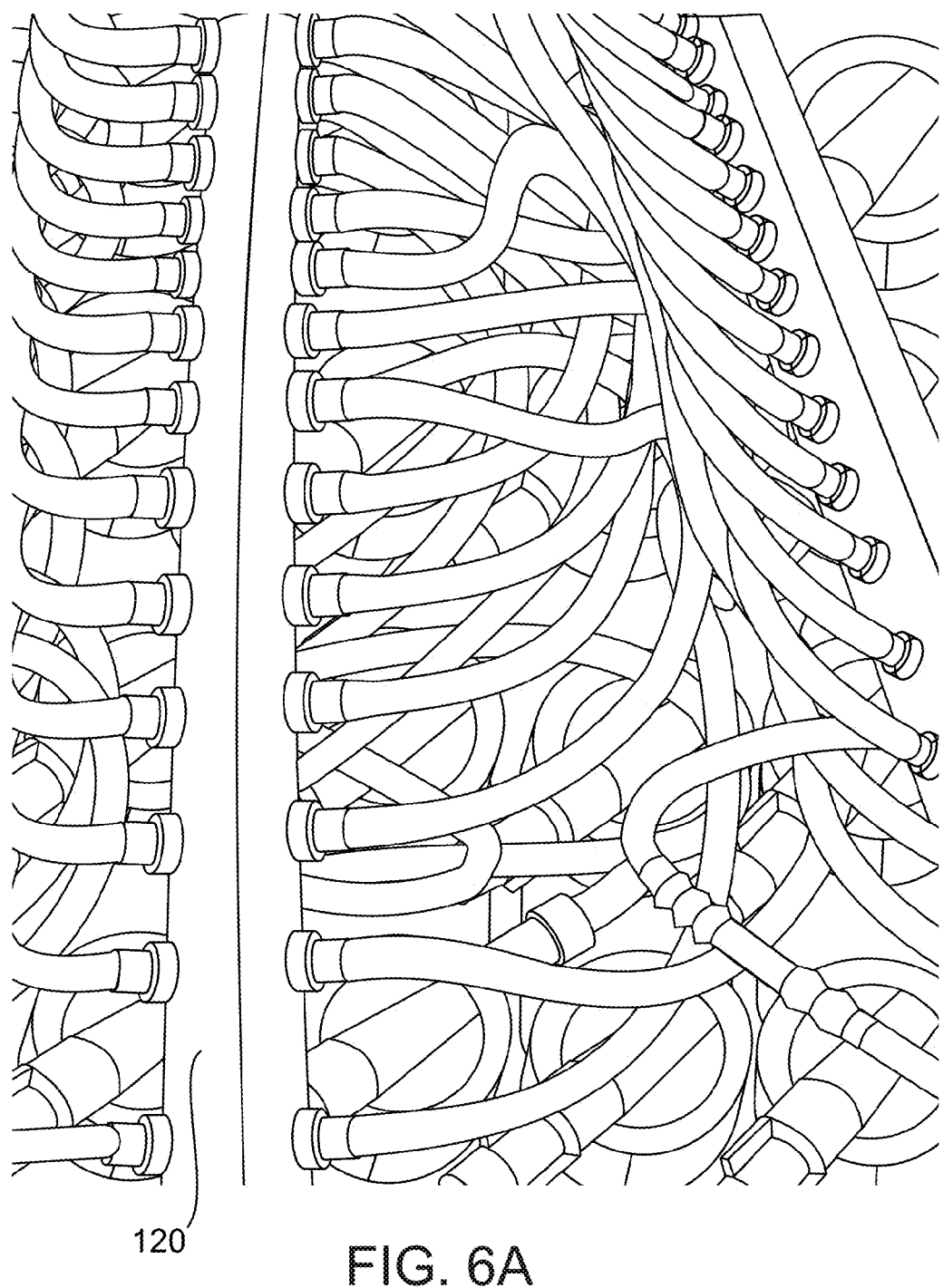
FIG. 6A is an external view of manifolds used to connect a large group of individual filters, according to an embodiment of the present invention.

FIG. 6A is an external view of manifolds used to connect a large group of individual filters 100, according to an embodiment of the present invention.

Figure 6B:
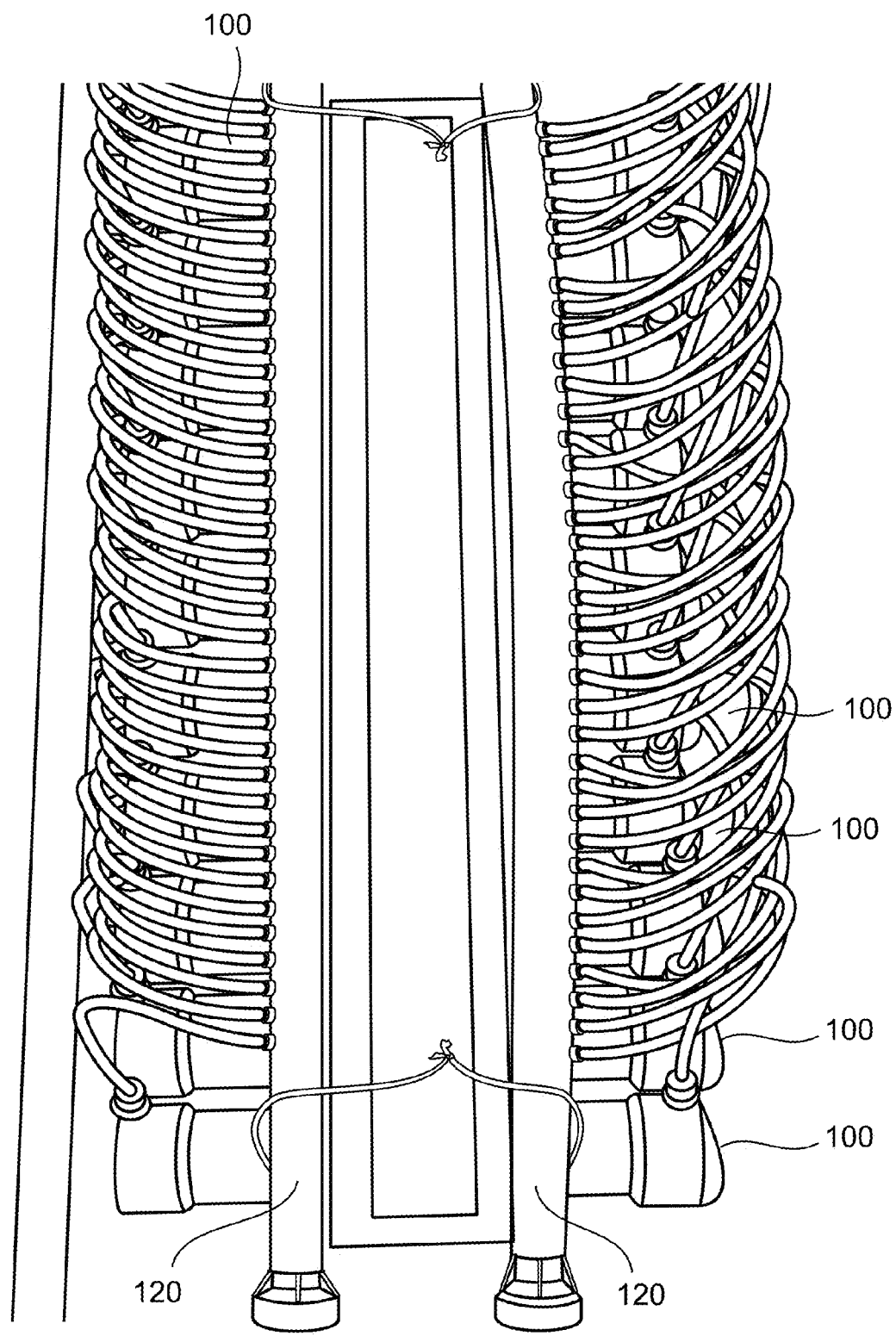
FIG. 6B is an external view of an additional configuration of a manifold used to connect a large group of individual filters, according to an embodiment of the present invention.

FIG. 6B is an external view of another configuration in which a manifold is used to connect a large group of individual filters 100, according to an embodiment of the present invention.

Figure 7:
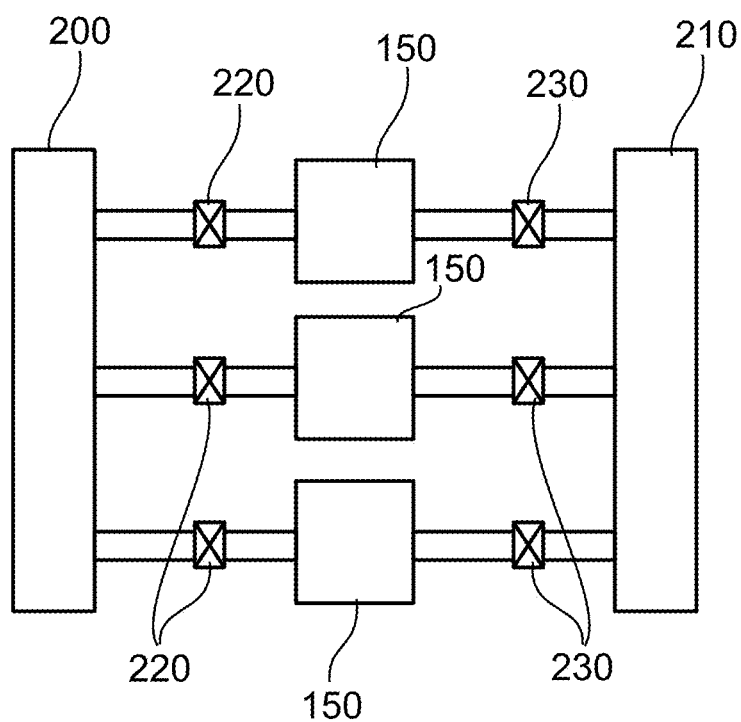
FIG. 7 is a simplified schematic of a group of groups of filters connected in parallel, according to an embodiment of the present invention.

FIG. 7 is a simplified schematic of a group of groups of filters connected in parallel, according to an embodiment of the present invention. For large capacity filtering installations, it may be convenient to connect a plurality of groups of filters in parallel, so as to achieve large throughput. Optional valves 220 and 230, if present, enable to isolate any group 150 as desired, to enable repair, cleaning through reverse flow or other cleaning, or for other purposes.

Figure 8A:
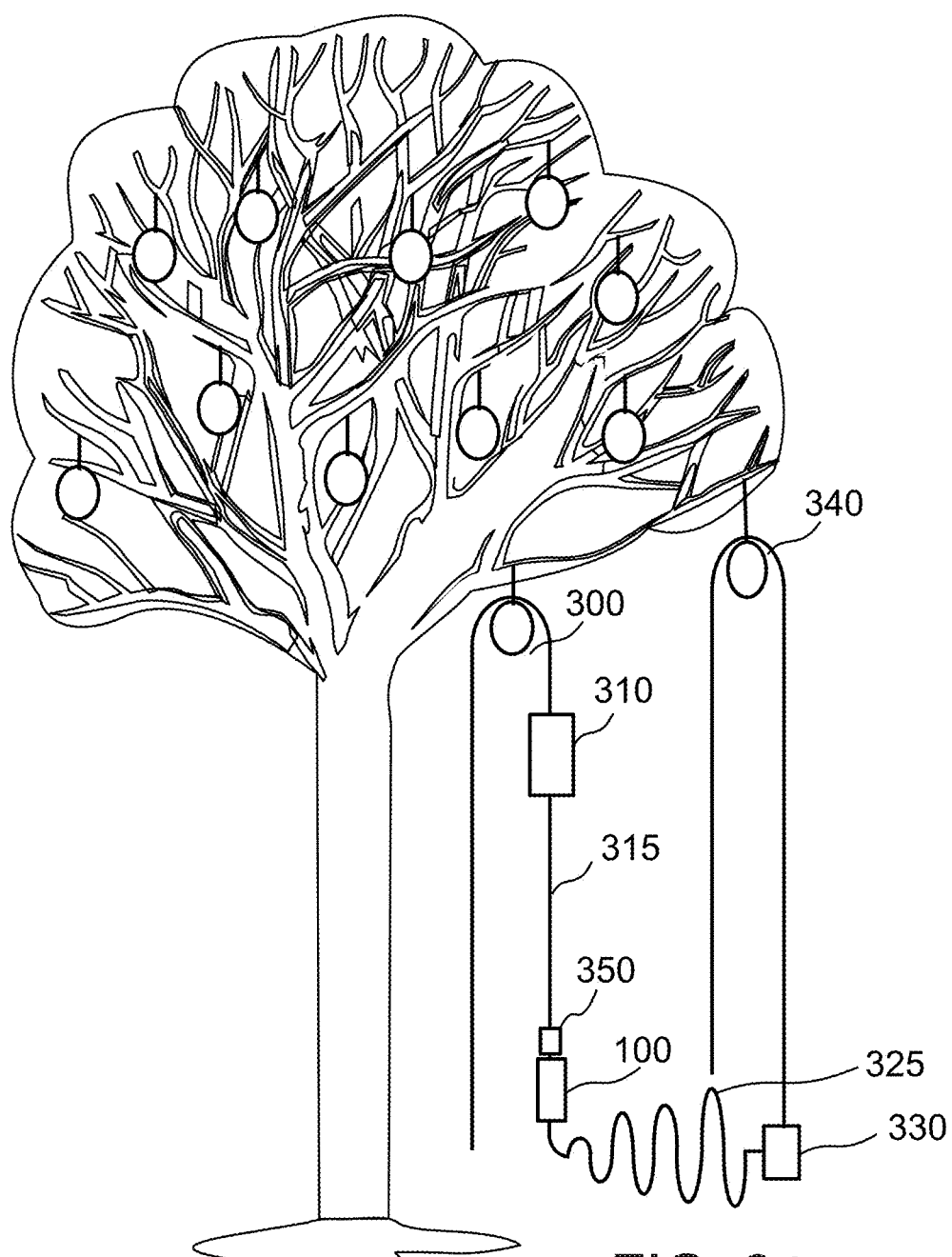
FIG. 8A is a simplified schematic of a water filtration system which does not require electric power for operation, according to an embodiment of the present invention.

FIG. 8 is a simplified schematic of a simple water filtering system which can be implemented without electricity, according to an embodiment of the present invention. A water input tank 310 is raised to a height using a pulley 300, or other mechanism. Input tank 310 might be, for example, a plastic jug or other simple container. Tubing between tank 310 and a filter 100 enables for a height differential to produce sufficient water pressure for filter 100 to function, providing a pure water source for environments where an electrically operated water filtration system is not practical. A group of filters 150 may be substituted for the single filter 100 shown in FIG. 8, if desired. The system may optionally be connected to a well, so that the same mechanism used for raising water from the well can further raise the water to produce the desired pressure at the filter level.

Optionally, additional tubing 325, an output tank 330 with faucet and a second pulley 340 may be provided. These additions make it possible to clean the filter, as described hereinabove, by providing back flow through the filter. Opening a valve (or simply disconnecting tubing 315 at point 350, and using pulley 340 to raise output tank 330 will provide back pressure through filter 100, cleaning the filter. Closing the line at 350, refilling tank 310, lowering tank 330 and raising tank 310 enables to continue filtering water with the cleaned filter 100.

In some embodiments, instead of using gravity for water pressure, a pump is used to provide pressure to flow water in the dialyzer or dialyzers. In some embodiments, the pump is a manual pump so that water can be treated without electricity. Optionally, the pump can be operated both manually and electrically. In some embodiments, the pump may be operated solar energy or heat (e.g. by fire) or steam.

FIG. 8B schematically illustrate a setup 800 for water filtration system which does not require electric power for operation, according to an embodiment of the present invention.

An impure water (e.g. polluted) from a source such a river 880 is pumped by manual or solar or heat or steam pump 802 and fed into a filtration apparatus using a dialyzer such as a discarded hemo-dialyzer 804 and the treated water is drained such as to a collecting vessel 806.

Low Cost Fitting

In some embodiments, extension tubes connected to inlet and/or outlet of a dialyzer are used for easy or convenient connection with water source and/or drain or flexibility in assembly of the water treatment apparatus. In some cases or embodiments, the dialyzer inlet and/or outlet are formed as rigid tubes such as about 15 mm OD (and about 10 mm ID). Therefore, in some embodiments of the invention, in order to flexibly connect the dialyzer to a water source or drain an extension tube narrower than the dialyzer inlet and/or outlet is used, wherein optionally a flexible tube is used.

In some embodiments, an in order to assist or support a connection the inlet and/or outlet of a dialyzer is fitted with a low cost tube or ring. For convenience, the dialyzer inlet and/or outlet, or tube fitted thereon, are referred to also as 'duct'.

In some embodiments, duct or ducts of a dialyzer are connected or fitted with an extension tube, and the tube is further connected to a water treatment apparatus, such as to a source of impure water or sewage pipe and/or water drainage pipe after treatment. For example, a flexible extension tube is fitted into a dialysate inlet and/or a dialysate outlet of a discarded hemo-dialyzer and provides connection with water supply and/or drain.

In some embodiments, the extension tube connection is sealed to or forms a seal with the duct. In some embodiments, the connection is carried out via another member or members (hereinafter also 'adapter') for matching the diameter of the extension tube with the diameter (or width) of the dialyzer duct. In some embodiments, the adapters are low cost components optionally made by adapting existing components such as by drilling and/or filing.

FIG. 9 schematically shows a flexible small diameter tube 3, equipped with a connection device (adapter) 1 and inserted into a hollow member (adapter) 2, according to an embodiment of the present invention. A small diameter refers to a diameter narrower than that of a dialyzer duct.

Figure 10:
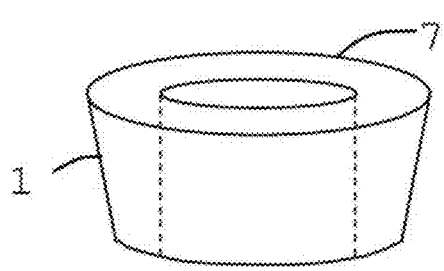
FIG. 10 schematically shows the connection device as of FIG. 9, according to an embodiment of the present invention.

FIG. 10 schematically shows adapter 1 of FIG. 9 as a conical device having a hollow 7 therethrough, where, in some embodiments, adapter 1 is a conical rigid member of a width (maximal diameter or average diameter) smaller than that of a dialyzer duct to be connected with.

Figure 11:
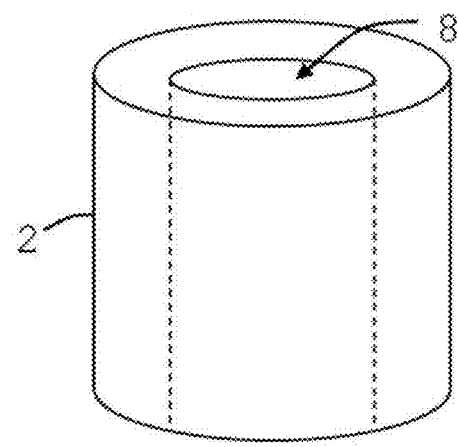
FIG. 11 schematically shows the hollow member as of FIG. 9, according to an embodiment of the present invention.

FIG. 11 schematically illustrates adapter 2 of FIG. 9 a member having a hollow 8, where, in some embodiments, adapter 2 is a flexible member and having a width (diameter) about yet smaller than that of a dialyzer duct to be connected with.

In some embodiments, adapter 1 may be obtained by cutting any commercially available conical test tube. In some embodiments, adapter 2 may be obtained by cutting a short segment of a larger diameter flexible tube (larger that that of adapter 1), whereby, in some embodiments, the ID of the large diameter flexible tube equals the OD of the small diameter flexible tube 3. In some embodiments, as optionally a particular or precise diameter of tube 3 is not mandatory or necessary, flexible tubes 3 may be obtained such as from discarded waste of a hemo-dialysis center or from plumbing equipment or as a commodity product.

In some embodiments, adapter 1 is inserted into an end of small diameter flexible tube 3 (e.g. front end), dilating said tube front end (dilated zone shown as 4). In some embodiments, adapter 1 is forced into tube 3 by force, thereby dilating front end 4 and securing adapter 1 therein. Optionally, in some embodiments, instead of using an adapter to dilate tube 3 at an end thereof, the tube is otherwise dilated and hardened such as by heat and/or impregnation with other material, optionally formed on a mold. Optionally or alternatively, another tube with a wider or dilated end is fitted in or on tube 3 to provide a wide section used as described below.

In some embodiments, tube 3 is inserted (e.g. from back end thereof opposite the dilated zone) into hollow 8 of adapter 2 wherein adapter 2 is wider than dilation 4, such that adapter 1 is loosely enclosing tube 3 proximal to dilated region 4, thereby forming a connection assembly used as described below.

Figure 12:
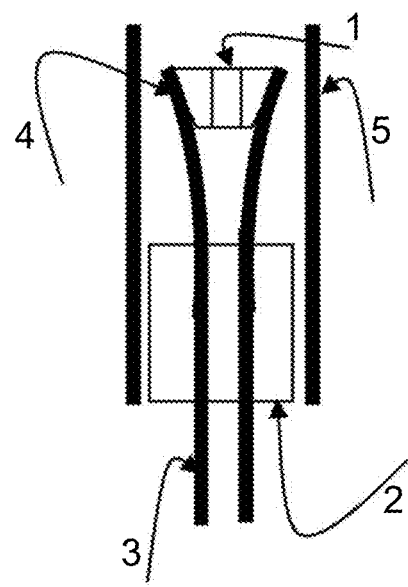
FIG. 12 schematically shows a connection assembly loosely of FIG. 9 inserted into a large diameter tube as a dialyzer inlet or outlet, according to an embodiment of the present invention.

FIG. 12 schematically shows a connection assembly of tube 3 and adapters 1 and 2 loosely inserted into a dialyzer inlet or outlet (duct) 5, according to an embodiment of the present invention.

In some embodiments, the connection assembly of tube 3 and adapters 1 and 2 is loosely inserted into a dialyzer inlet or outlet (duct) 5 of a diameter about or somewhat larger than the width or diameter of adapter 2. Subsequently, tube 3 equipped with adapter 1 (or otherwise dilated) is pulled, optionally forcefully, towards adapter 2 (e.g. pulled back or out of duct 5) while keeping adapter 2 immobile or maintaining the position of adapter 2 (at least relative to the moving tube 3) such as by gripping the duct about adapter 2. Thus, dilated front end region 4 of tube 3 slides into hollow 8 of adapter 2. Adapter 2 being a flexible member, hollow 8 thereof is dilated and presses against the inner wall of duct 5, providing a sealing contact 6 with duct 5. Fluid passage is provided to the dialyzer via duct 5, hollow 7 of adapter 1 and lumen (inside cavity) of tube 3.

Figure 13:
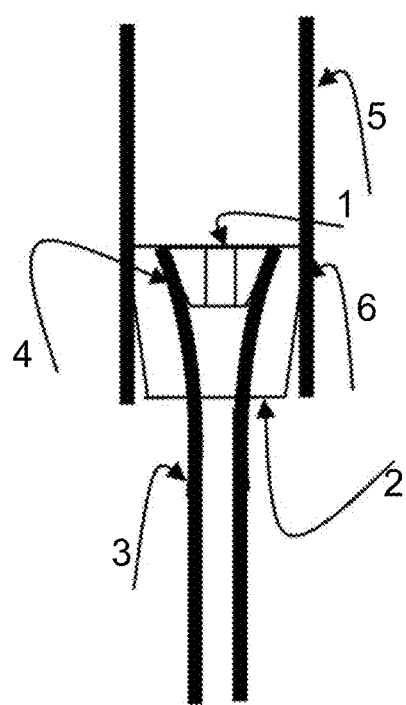
FIG. 13 schematically shows a connection assembly as of FIG. 9 after being pulled back, providing a sealing surface which presses against the inner wall of a large diameter tube such as dialyzer inlet or outlet, according to an embodiment of the present invention.

FIG. 13 schematically shows the connection assembly after being pulled back, providing a sealing surface which presses against the inner wall of a dialyzer duct, according to an embodiment of the present invention.

Once flexible tube 3 is locked in and presses on the duct (sealed with) a dialyzer duct, flexible tube 3 may be connected to a source or drain of water. In some embodiments, a plurality of dialyzers are connected with a plurality of tubes 3 into a manifold providing source of impure water and/or drain of treated water.

In some embodiments, tube 3 connects to water source or drain pipe or manifold via a hole cut into the pipe, optionally via an intermediary hollow stub (tube) connecting between the hole in the pipe and tube 3. The connection is optionally by adhesive, where an exemplary embodiment is described below.

In some embodiments, two tubes of different diameters are connected by inserting a first tube having dilation (e.g. wider diameter) at an end thereof into a wider tube having the opening, and pulling the first tube out of the opening, thereby pressing the dilation on the walls of the wider tube.

In some embodiments, the wider tube diameter narrows towards the end thereof, and the first tube is squeezed at the dilated end thereof in order to push the dilated part into the wider tube.

In some embodiments, the diameter of the first tube widens towards an end thereof, and by squeezing the wider end thereof is inserted into the wider tube, and by pulling the first tube back the wider part thereof presses against the walls of the wider tube.

Figure 14:
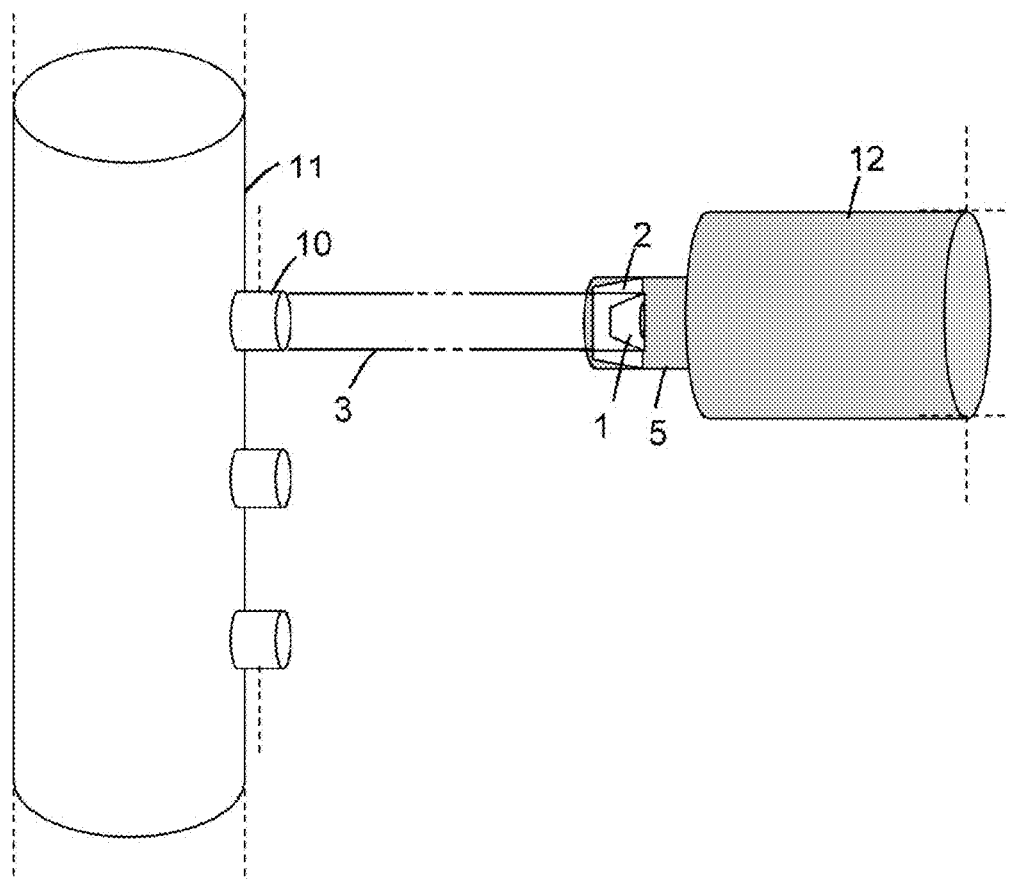
FIG. 14 schematically shows a dialyzer connected to a water manifold, according to an embodiment of the present invention.

FIG. 14 schematically shows a dialyzer 12 connected to a water manifold (e.g. pipe) 11 through tube 3, according to an embodiment of the present invention. In some embodiments, tube 3 connects to manifold 11 via stub tubes 10 (e.g. tubes inserted in holes in the manifold pipe), whereas in some embodiments, tube 3 connects to manifold 11 directly into holes therein without intermediary stubs 10.

The structure of the dialyzer and the manifold are for illustration only and the dashed lines represents optional or probable or possible extensions, e.g. tube 3 may be longer that relatively illustrated or the number of stubs 10 may be larger, or the dialyzer may be connected to manifold 11 by more that one duct 5.

In some embodiments, tubes such as tube 3 are connected to a pipe or manifold, such as manifold 11 of FIG. 14, directly into holes formed therein (dispensing with intermediaries such as stub tubes 10 of FIG. 14).

Figure 15:
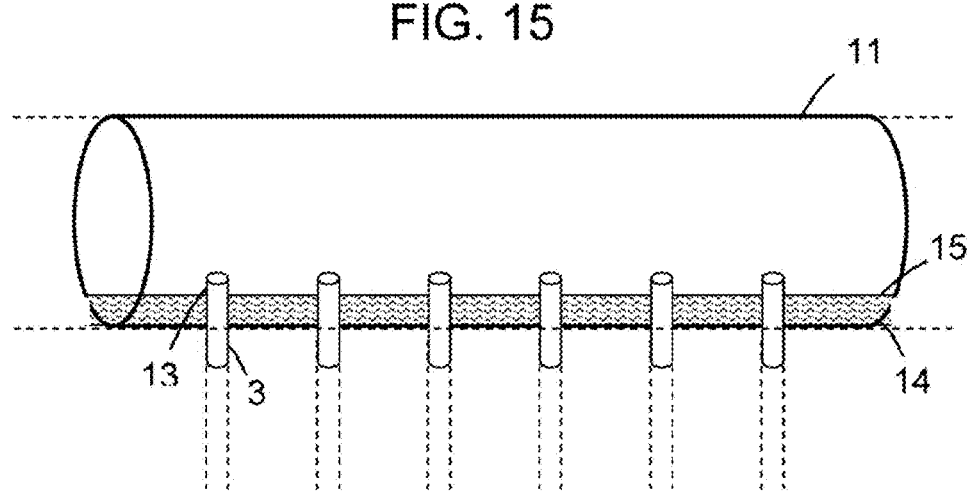
FIG. 15 schematically shows a method of connecting tubes to water manifold by potting, according to an embodiment of the present invention.

FIG. 15 schematically shows a method or technique of connecting tubes 3 to water manifold 11 by potting, according to an embodiment of the present invention.

In some embodiments, holes are drilled or formed in manifold 11 (i.e. a pipe to be formed as a manifold) and end portions 13 of dialyzers (e.g. tube 3) are inserted therein, while sticking to some distance into the hollow of manifold 11. Manifold 11 is disposed generally horizontally with ends portions of tubes 13 generally at the bottom side 14. An adhesive 15 having rheological properties (e.g. viscosity) such that the adhesive spreads and levels (e.g. self leveling) is administered into the bottom side 14 of the hollow of manifold 11 such that adhesive 15 spreads around the tubes 3 while ends thereof are above the level of adhesive 15 ('potting'). When adhesive 15 dries and/or cures, tubes 3 are bonded to manifold 11. Dashed lines indicate optional or possible extension, e.g. of tubes 3 or pipe (manifold) 11.

Some Exemplary Methods

Figure 16:
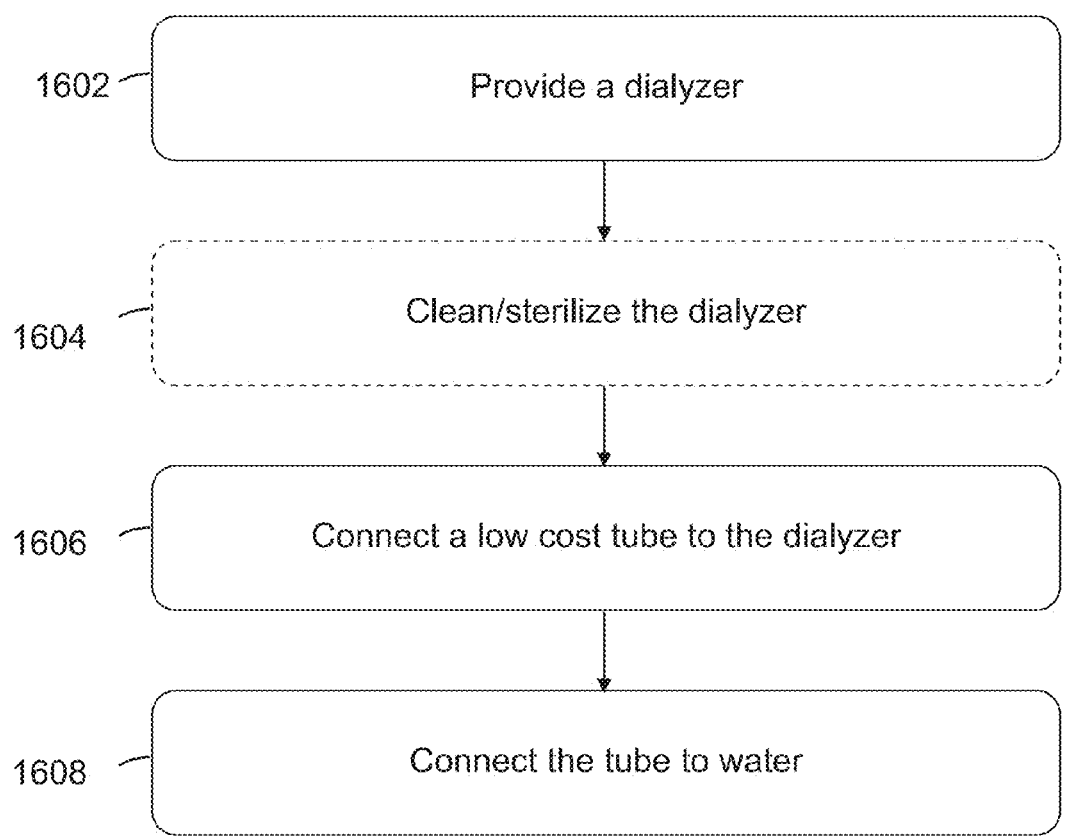
FIG. 16 schematically illustrates an outline of operations for connection of a dialyzer for water treatment, according to an embodiment of the present invention.

FIG. 16 schematically illustrates an outline of operations for connection of a dialyzer for water treatment, according to an embodiment of the present invention.

A dialyzer such as a discarded hemo-dialyzer is provided (1602). In some embodiments, if the dialyzer is contaminated or polluted or otherwise unhygienic the dialyzer is cleaned and/or sterilized or otherwise sanitized (1604).

The inlet and/or outlet (duct) of the dialyzer is connected to or fitted with a low cost tube (1606), such as discarded a tube from dialysis centers or other medical equipment (optionally sterilized or otherwise sanitized) or cut out from plumbing equipment. The tube is connected to water source or drain (1608) such as to a sewage pipe.

Figure 17:
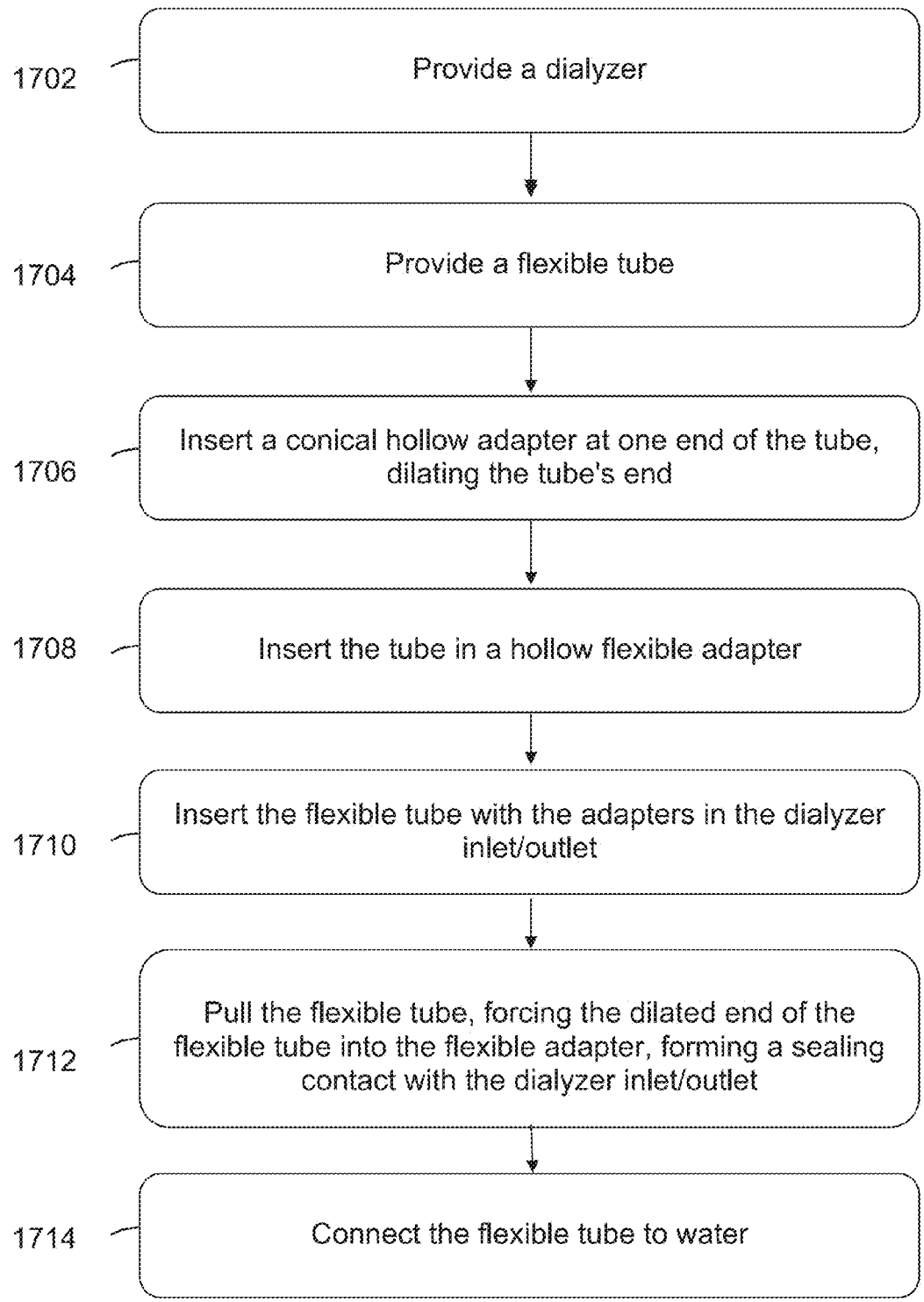
FIG. 17 schematically illustrates operations for connection of a dialyzer for water treatment, according to an embodiment of the present invention.

FIG. 17 schematically illustrates operations for connection of a dialyzer for water treatment, according to an embodiment of the present invention.

A dialyzer such as a discarded hemo-dialyzer is provided (1702). In some embodiments, if the dialyzer is contaminated or polluted or otherwise unhygienic the dialyzer is cleaned and/or sterilized or otherwise sanitized.

A flexible tube such as a discarded a tube from dialysis centers or other medical equipment or obtained as a commodity is provided (1704).

A hollow conical member (adapter) is inserted at one end of the flexible tube, thereby dilating the tube about that end (1706), and the tube is inserted (at opposite end thereof) into a hollow flexible member (adapter) (1708).

The flexible tube with the adapters is inserted into an inlet or outlet (duct) of a dialyzer with the dilated end facing the dialyzer (1710). Subsequently, the flexible tube is pulled in a direction out of the duct, forcing the dilated end with the conical adapter into the hollow of the flexible adapter, thereby dilating the hollow of the flexible member and forming a sealing contact with the walls of the duct (1712).

The flexible tube is connected to water source or drain (1714) such as to a sewage pipe, optionally via or with an intermediate such as to remove debris or other particles, optionally to prevent damage to the system and particularly the dialyze.

Figure 18:
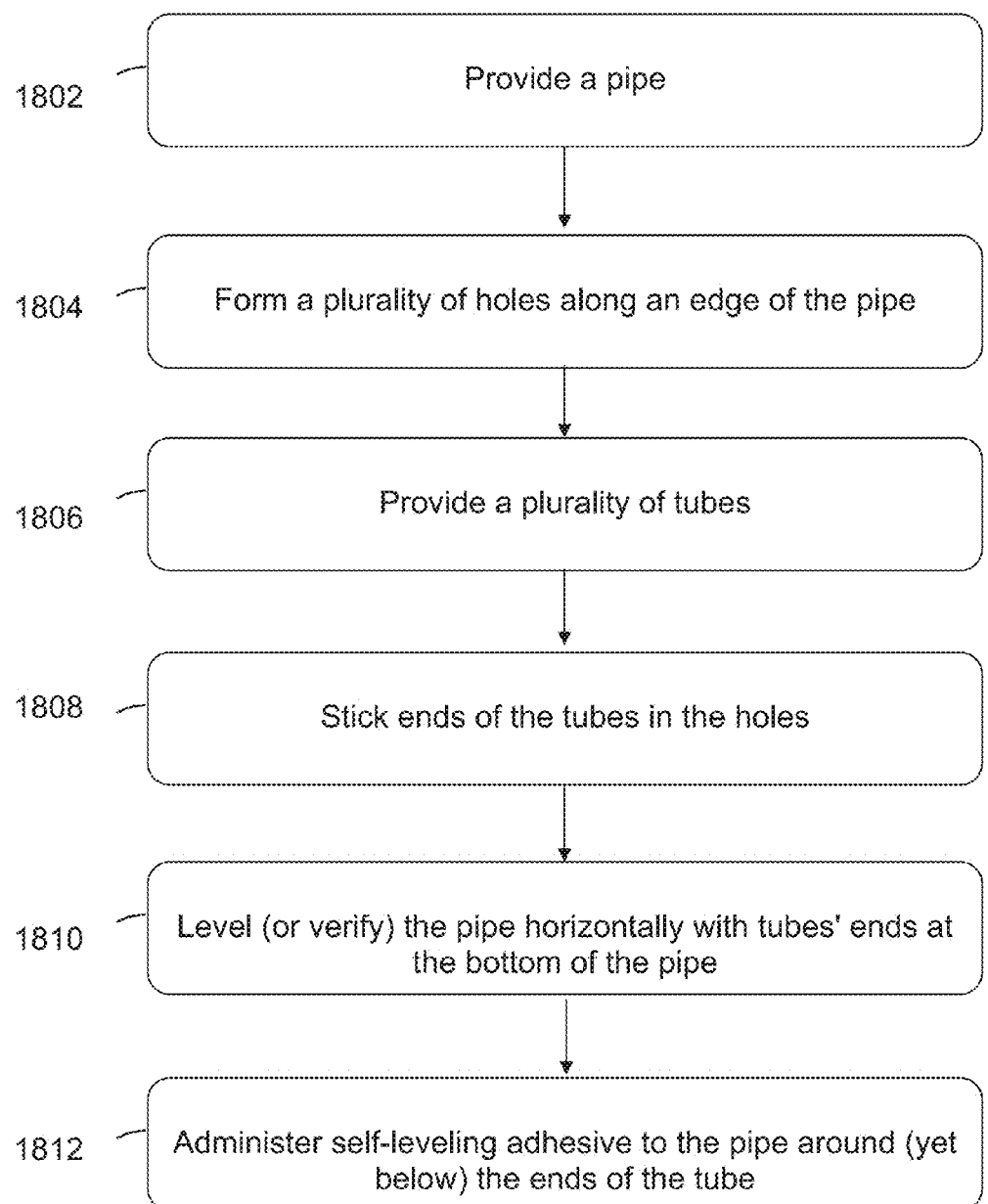
FIG. 18 schematically illustrates an outline of operations for connecting tubes to a pipe in order to connect dialyzers for water treatment to the pipe, according to an embodiment of the present invention.

FIG. 18 schematically illustrates an outline of operations for connecting tubes to a pipe (e.g. forming a manifold) in order to connect dialyzers for water treatment to the pipe, according to an embodiment of the present invention.

A pipe is provided or accessed (1802), such as pipe or conduit for water source or drain.

A plurality of holes is formed along an edge of the pipe (1804), such as by drilling, machining or any method of the art.

A plurality of tubes (e.g. corresponding to the number of holes) is provided (1806) and end portions of the tubes are inserted into the holes (1808) such that the tubes' end portions extend in the pipe by an interval (e.g. a determined interval marked on the tubes) smaller than the pipe's diameter. In some embodiments, the tubes are low cost, such as a commodity.

The pipe is leveled (or checked for leveling) generally horizontally such that the tubes end portions are generally at the bottom of the pipe (1810), and a self-leveling (e.g. of low viscosity or thin) adhesive is administered to the pipe generally at the bottom, letting the adhesive to spread around (but not over) the tubes' ends (1812). As the adhesive dries and/or cures the pipe with the tubes forms a manifold, such as for water treatment with a plurality of dialyzers.

Subsequently, in some embodiments, the tubes are connected to ducts of dialyzers and, in some embodiments, the pipe serves as a source of impure water and/or drain for treated water or a conduit thereof.

The methods and techniques described above are not limited for connection of dialyzers and, in some embodiments, may be employed for connection other tubes of different diameters or forming manifolds by low cost components.

In some embodiments, the flow is reversed, e.g. drain is used as a water source, to clean the system such as the membranes, such as described above.

Kit

Figure 19:
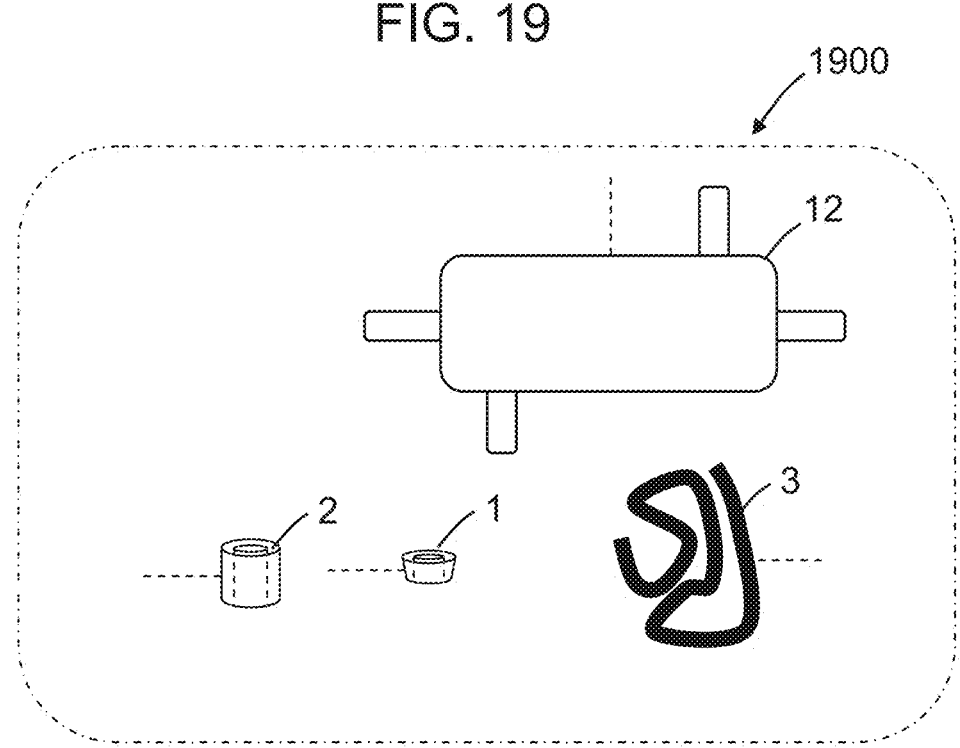
FIG. 19 schematically illustrates a kit for assembly in a water treatment apparatus, according to an embodiment of the present invention.

FIG. 19 schematically illustrates a kit 1900 for assembly in a water treatment apparatus, according to an embodiment of the present invention.

Kit 1900 comprises a dialyzer 12 (e.g. as that of FIG. 14), a flexible tube 3 (e.g. as that of FIG. 9) and adapters 1 and 2 (such as in FIGS. 10 and 11, respectively).

Dialyzer 12, flexible tube 3 and adapters 1 and 2 represent a plurality of the respective items, as indicated by the dashed lines.

In some embodiments, the number of items in kit 1900 is determined such as to enable assembly or construction of a water treatment apparatus as, for example, described above.

In some embodiments, tube 3 is optional as it can be obtained from commodity or waste materials. In some embodiments, adapter 1 is optional as tube 3 may be dilated (widened) as described above.

Exemplary Experimental Results

Secondary effluent water was treated with hemo-dialyzers by apparatus and method such as described above using a FRESENIUS dialyzer (Fresenius Medical Care Holdings, Inc) providing treated tertiary effluent water. Likewise, for comparison control, the secondary effluent water was treated with sand filtration of a municipal authority.

Comparisons of properties of the tertiary effluents obtained by the two

TABLE I

| Test I | UUF Tertiary Effluent (Dialyzer Membrane) | Municipal Tertiary Effluent (Sand filter) |
|---|---|---|
| Coliform (fecal bacteria) per 100 ml | 10< | 2,300 |
| BOD (Biological Oxygen Demand)( | 0.6 | 2.5 |
| TKN Sum of organic nitrogen) ( | 1.6 | 3.1 |
| NTU (Turbidity) | 0.22 | 0.68 | treatments are compared in Table I and Table II below.

TABLE II

| Test II | UUF Tertiary Effluent (Dialyzer Membrane) | Municipal Tertiary Effluent (Sand filter) |
|---|---|---|
| Coliform (fecal bacteria) per 100 ml | 1< | 400 |
| BOD (Biological Oxygen Demand)( | 0.7 | 2.0 |
| TKN Sum of organic nitrogen) ( | 7.2 | 13.9 |
| NTU (Turbidity) | 0.24 | 1.07 |

The tables demonstrate that using a dialyzer yield better water treatment, with respect to various parameters (e.g. pathogen clearance, turbidity, BOD or TKN) as compared to a municipal water treatment facility. The treatment with the dialyzer was carried out with about 0.3 to 0.5 working pressure (trans-membrane pressure) with an output of about 3.0-4.5 cubic meters per hour.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for water purification comprising:
   a) supplying a medical hemodialysis filter having a plurality of capillary membranes each having an inside of the capillary and an outside of the capillary, and two flow paths separated by said capillary membranes, a first flow path on the inside of said capillary membranes and a second flow path on the outside of said capillary membranes;
   b) providing polluted water under pressure on an inside of said capillary membrane, and
   c) withdrawing clean water from an outside of said capillary membrane.

2. The method of claim 1, wherein substantially all of said polluted water is withdrawn in said clean water.

3. The method of claim 1, further comprising:
   d) backwashing said medical hemodialysis filters including:
      i) injecting said clean water on said outside of said capillary membrane, and
      ii) withdrawing said clean water and accumulated material from said inside of said capillary membrane.

4. The method of claim 1, further comprising:
   d) connecting a plurality of medical hemodialysis filters in parallel, and wherein said providing and said withdrawing are from said plurality of medical hemodialysis filters.

5. The method of claim 4, wherein said connecting includes:
   i) providing a tube with a plurality of holes;
   ii) inserting an end portion of each of said plurality of medical hemodialysis filters into a corresponding hole of said plurality of holes, and
   iii) administering a self leveling adhesive into said tube.

6. The method of claim 4, further comprising:
   e) forming said plurality of medical hemodialysis filters into a plurality of groups, and
   f) isolating at least one group of said plurality of groups from another group of said plurality of groups with at least one valve.

7. The method of claim 6, further comprising:
   g) providing clean water from an output of at least one group of said medical hemodialysis filters to an output of at least another one group of said medical hemodialysis filters so as to clean said another group of medical hemodialysis filters by backwashing.

8. The method of claim 1, wherein said medical hemodialysis filter includes a used medical hemo-dialysis filter and further comprising:
   d) cleaning and sterilizing said used medical hemodialysis filter.

9. The method of claim 1, wherein said providing of said polluted water is at a rate of at least 3 cubic meters per hour.

10. The method of claim 1, further comprising;
    d) using said clean water for at least one use selected from the group consisting of municipal, drinking, and commercial.

11. The method of claim 1, wherein said medical hemodialysis filter comprises a used medical hemodialysis filter.

12. The method of claim 1, wherein said medical hemodialysis filter comprises a medical hemodialysis filter discarded from medical use.

13. The method of claim 1, wherein said medical hemodialysis filter comprises an unused medical hemodialysis filter discarded from medical use.

14. The method of claim 1, wherein said providing of said polluted water under pressure is under at least 0.5 Bar pressure.

15. The method of claim 1 wherein said providing polluted water comprises providing said polluted water to two openings in said medical hemodialysis filter—to a blood-in opening and to a blood-out opening.

* * * * *